United States Patent

Alexay et al.

Patent Number: 5,519,219
Date of Patent: May 21, 1996

[54] PORTABLE FILTER INFRARED SPECTROMETER

[75] Inventors: Christopher C. Alexay, Walpole, N.H.; William L. Truett, Brattleboro; Christopher D. Prozzo, Athens, both of Vt.; Barry O'Dwyer, Harrisville, N.H.

[73] Assignee: Janos Technology Inc., Townshend, Vt.

[21] Appl. No.: 303,174

[22] Filed: Sep. 8, 1994

[51] Int. Cl.⁶ .................................................. G01N 21/25
[52] U.S. Cl. .......................... 250/339.07; 250/339.11; 356/51
[58] Field of Search .................... 250/339.07, 339.11, 250/339.12, 341.8; 356/51

[56] References Cited

U.S. PATENT DOCUMENTS

| | | | |
|---|---|---|---|
| 3,811,781 | 5/1974 | Lowy | 356/188 |
| 4,527,062 | 7/1985 | Novinson | 250/339.11 |
| 4,560,275 | 12/1985 | Goetz | 250/339.07 |
| 4,629,322 | 12/1986 | Pollard | 356/300 |
| 4,647,777 | 3/1987 | Meyer | 250/339.11 |
| 4,825,076 | 4/1989 | Shields | 250/343 |
| 5,036,198 | 7/1991 | Spaeth | 250/343 |
| 5,134,291 | 7/1992 | Ruhl, Jr. et al. | 250/339.11 |
| 5,166,755 | 11/1992 | Gat | 356/419 |

FOREIGN PATENT DOCUMENTS 1376717  2/1991  Russian Federation .......... 250/339.07

*Primary Examiner*—Davis L. Willis
*Assistant Examiner*—Richard Hanig
*Attorney, Agent, or Firm*—Herbert M. Wolfson

[57] ABSTRACT

There is described within a portable, battery-powered multiple filter infrared spectrometer consisting of a highly efficient optical system employing an infrared source with a chopper, from which IR energy passes through compound parabolic concentrators (CPC's) and is directed by a beamsplitter to the external sample, where the beam intersects with the sample via reflection and is returned through the CPC and beamsplitter to a stationary filter assembly and discrete detector array where the energy is converted to an A.C. (alternating current) signal. This current energizes an LED bar graph display for spectral identification. This method and apparatus is used to determine IR spectra of solids, liquids on a mirror, and gases in a container with a mirror to reflect light.

4 Claims, 3 Drawing Sheets

PORTABLE FILTER INFRARED SPECTROMETER

BACKGROUND OF THE INVENTION

This invention relates to the field of spectrometry; in particular, it concerns the qualitative and quantitative analysis of sample materials using single beam multiple wavelength analysis method.

Such spectrometers have in the past been based on a scanning device employing a dispersive element, such as a prism or grating, or use of the Fourier Transform-Michelson interferometer to generate a spectrum. A spectrometer introduced in the early 1970's employed a circular variable filter which, upon rotation, generated a complete spectrum from 2.5–14.5 microns utilizing three filter segments. This spectrometer was capable of determining the concentrations of virtually all IR absorption gases over a range of concentration of several percent to 1 part per million. Later this spectrometer was placed under microprocessor control which made measurement and readout possible in all mid-IR wavelengths.

Other filter spectrometers in use in the mid-IR employ discrete filters for the measurement of a particular chemical species, such as hydrocarbon-in-water measured post extraction at 3.4 microns, and carbon dioxide gas at 4.25 microns.

These aforementioned spectrometers have one thing in common: they perform a quantitative measurement of a species of chemical, or several measurements of this type. They are not employed to perform qualitative identifications of organic and inorganic molecules, despite the necessity for qualitative identifications in the work of the majority of analytical laboratories and in a broad variety of field analysis needs, such as in the disciplines of geology, materials recycling, archaeology, etc.

In addition, many commercially available spectrometers include filters on a rotating wheel which is moved during each observation period, thus creating a problem of instability as well as the need for large areas of filter material, which raises the cost of such devices.

Accordingly, it is the object of the present invention to provide a multiple wavelength spectrometer of a portable size for use in the field to obtain qualitative identification of all solids, liquids, and gases.

Another object of this invention is to provide such a spectrometer which offers an exceptional signal-to-noise ratio in a very small device, allowing accuracy, stability, and cost-effectiveness. This object is accomplished in the present invention with the use of highly efficient compound parabolic concentrators which produce an exceptional signal-to-noise ratio, and a very stable stationary set of filters.

SUMMARY OF THE PRESENT INVENTION

In accordance with the present invention, a portable battery-powered instrument is provided which utilizes a highly efficient optical system with an IR source, a chopping mechanism to chop the light from the source, a compound parabolic concentrator (CPC) to direct the IR beam to a beamsplitter, which then redirects the IR beam through another CPC to the sample. The sample can be a solid, or a liquid on a mirror, or a gas in a container with a mirror to reflect back the light. From the sample, the IR beam is reflected back through the CPC and beamsplitter to a stationary assembly of filters and detectors. The group of filters includes filters from 2–13 microns in wavelength. The discrete detector array provides one detector for each filter. The detectors then convert the light to an electrical signal. Since the signal is chopped, an Alternating Current (A.C.) is produced. This current is used to drive a set of LED bar graphs. The pattern of the bar graph display can be interpreted to identify the sample in the IR beam.

DETAILED DESCRIPTION OF THE PREFERRED EMBODIMENT

Figure 1:
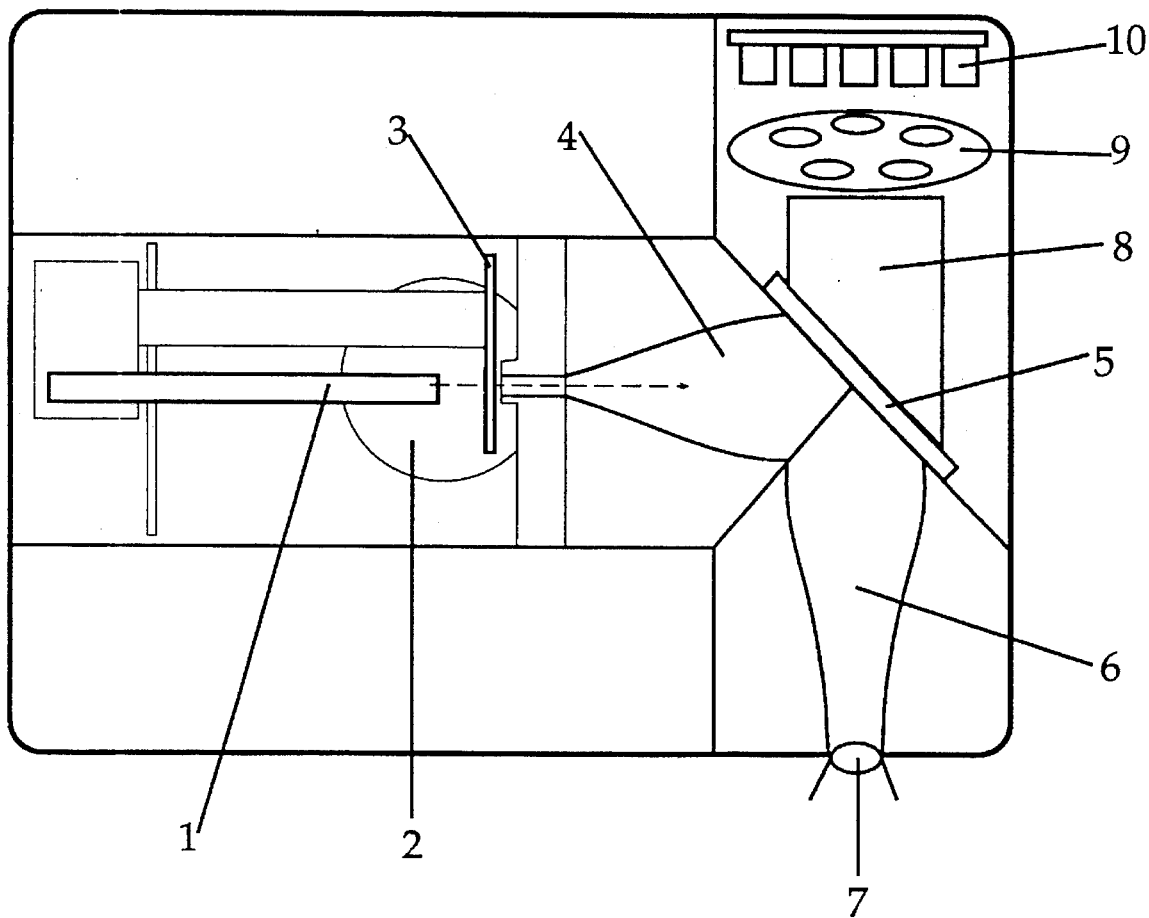
FIG. 1 is a simplified diagrammatic illustration of the portable filter infrared spectrometer apparatus in accordance with the present invention.

Referring now to FIG. 1 of the drawings, a simplified diagram of a filter infrared spectrometer apparatus embodying the principles of this invention is provided. The spectrometer includes an infrared source 1 which is focused by an spherical cavity 2. The chopper 3 mechanically interrupts the IR beam so that the beam is mechanically interrupted at regular intervals. The compound parabolic concentrator (CPC) 4 funnels the focused light from the source and diffuses it to the beamsplitter 5. The beamsplitter 5 then directs the beam of IR light through another CPC 6, which concentrates the IR beam onto the sample aperture 7, where the IR beam emerges from the device and falls upon the sample which may be a solid, liquid, or gas. The IR beam is then reflected from the sample aperture 7 back through CPC 6, which passes the beam through the beamsplitter 5 and cylindrical cavity 8 to arrive on the stationary filter array assembly 9. The filter array 9 contains up to twelve filters, through which the IR light passes onto an array of detectors 10 equal to the number of filters 9. The detector array 10 converts the IR beam to an alternating current which is amplified and used to drive an LED bar graph, or other suitable display of the energy which is falling on each detector.

Figure 2:
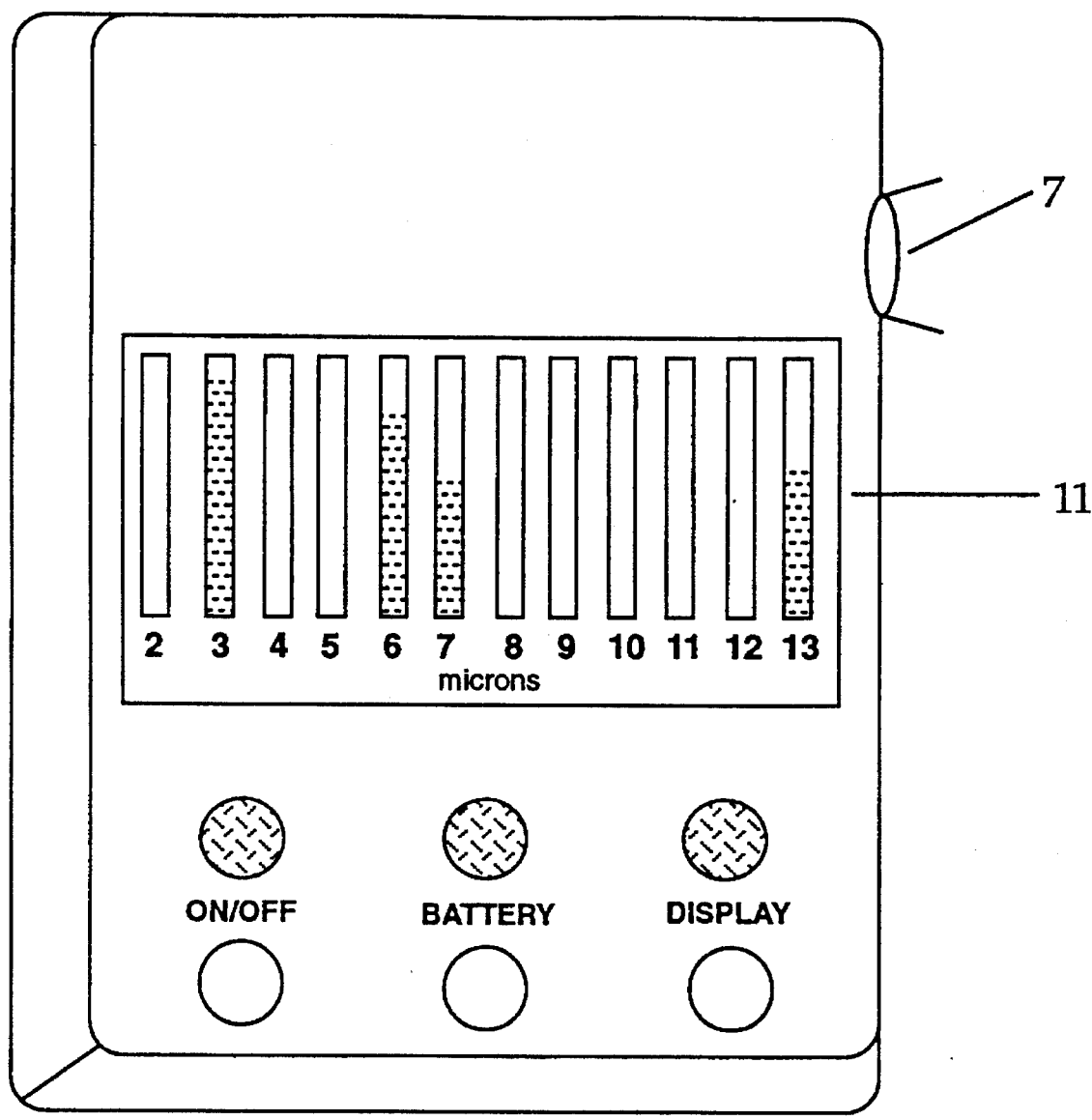
FIG. 2 is a front view of the external case and LED bar graph readout included in the present invention.

Now referring to FIG. 2, the present invention is illustrated with its external case and LED bar graph display. The sample aperture 7 is placed above the sample to be measured and the IR beam is then reflected back into the instrument where it is transformed into a pattern on the LED bar graph display 11 which the user may then interpret for substance identification.

Figure 3:
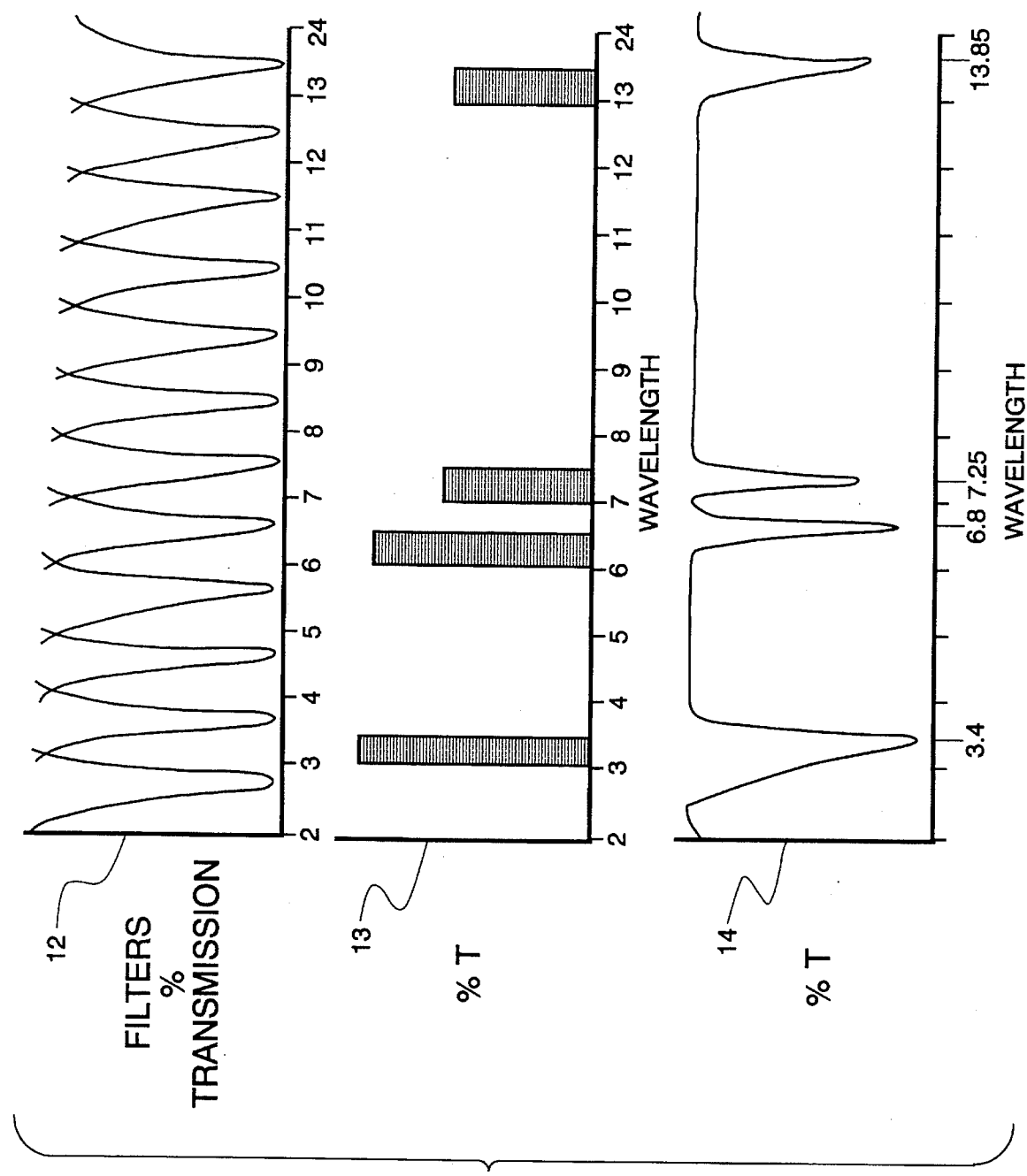
FIG. 3 is an explanation of interpretation of the LED bar graph readout.

The method of interpretation is illustrated in FIG. 3. This method is possible because all materials show a characteristic spectral pattern. An example of Polyethylene is used here. Using 10–12 filters, shown in filter diagram 12, a complete pattern is generated by means of the aforementioned mechanisms in the present invention. The representation of this pattern is illustrated in the bar graph display 13 of Polyethylene. The bar graph display 13 corresponds to an actual spectrum 14 of the sample (Polyethylene in this case.)

We claim:

1. A portable device for determining the IR spectra of solids, liquids, and gases consisting essentially of:

a. an IR source concentrated into a narrow beam of energy by use of a spherical optical cavity;

b. a compound parabolic concentrator adapted to receive said narrow beam, the light being periodically interrupted by means of an optical chopper which is positioned between the source and the compound parabolic concentrator, energy emergent from said source is directed to and from the sample by compound parabolic concentrator;

c. said beam of energy falls on a beam splitter which directs about one-half of the energy to a compound parabolic concentrator in contact with a sample whose IR spectrum is to be determined, thence is reflected back as a reflected energy beam through said compound parabolic concentrator;

d. said reflected energy beam is directed to a stationary array of filters of various wavelengths;

e. energy emerging from said filter array is then directed onto a set of detectors for IR energy, the number of such detectors being equal to the number of filters in said filter array;

f. The output from the several detectors, after suitable amplification, is displayed on an appropriate read-out device, as a LED array or computer screen.

2. The device described in claim 1 having a general purpose set of filters over a range of 2–15 micron wavelengths.

3. The device described in claim 1 having a specific set of filters to identify plastics for use in recycling centers: 3.4, 5.7, 6.8, and 13.85 microns, in order to identify high and low density polyethylene and polyethylene terphthalate.

4. A portable device for determining the IR spectra of samples of solids, liquids and gases consisting essentially of:

a. an infrared source of light;

b. a spherical optical cavity positioned to receive light from said source and to concentrate said light into a narrow beam;

c. a first compound parabolic concentrator to receive said concentrated beam of light;

d. an optical chopper positioned between said source and said first concentrator to interrupt said light at regular intervals;

e. a beam splitter to receive concentrated light from said first concentrator and to reflect a portion thereof through a second compound parabolic concentrator positioned substantially at a right angle to said first concentrator adapted to focus said portion of light through an aperture onto a sample;

f. said sample adapted to reflect said portion of light back through said aperture and said second concentrator through said beam splitter onto a stationary array of filters for various wavelengths of light;

g. an array of detectors equal to the number of filters in said stationary array to receive said light from said filter array and to convert said light into an alternating current which, after amplification, is directed to read-out means.

* * * * *